(12) United States Patent
Wu et al.

(10) Patent No.: US 10,835,135 B2
(45) Date of Patent: Nov. 17, 2020

(54) NON-CONTACT HEARTBEAT RATE MEASUREMENT SYSTEM, METHOD AND APPARATUS THEREOF

(71) Applicant: NATIONAL CHIAO TUNG UNIVERSITY, Hsinchu (TW)

(72) Inventors: Bing-Fei Wu, Hsinchu (TW); Meng-Liang Chung, Changhua County (TW); Tsong-Yang Tsou, Taoyuan (TW); Yun-Wei Chu, Taichung (TW); Kuan-Hung Chen, Hsinchu (TW); Po-Wei Huang, Yunlin County (TW); Yin-Yin Yang, Taichung (TW)

(73) Assignee: NATIONAL CHIAO TUNG UNIVERSITY, Hsinchu (TW)

( * ) Notice: Subject to any disclaimer, the term of this patent is extended or adjusted under 35 U.S.C. 154(b) by 92 days.

(21) Appl. No.: 16/393,947

(22) Filed: Apr. 24, 2019

(65) Prior Publication Data
US 2019/0328246 A1    Oct. 31, 2019

(30) Foreign Application Priority Data
Apr. 25, 2018   (TW) .............................. 107114076 A

(51) Int. Cl.
*G06K 9/00*    (2006.01)
*A61B 5/024*   (2006.01)
(Continued)

(52) U.S. Cl.
CPC ........ *A61B 5/02416* (2013.01); *A61B 5/1128* (2013.01); *A61B 5/7207* (2013.01);
(Continued)

(58) Field of Classification Search
None
See application file for complete search history.

(56) References Cited

U.S. PATENT DOCUMENTS

| 9,750,420 | B1 * | 9/2017 | Agrawal | .................. G06T 7/73 |
| 2010/0205541 | A1 * | 8/2010 | Rapaport | .............. G06F 16/285 |
| | | | | 715/753 |

(Continued)

FOREIGN PATENT DOCUMENTS

| CN | 104168819 A | 11/2014 |
| TW | I331028 B | 10/2010 |

(Continued)

OTHER PUBLICATIONS

Ming-Zher Poh et al., "Advancements in noncontact, multiparameter physiological measurements using a webcam," IEEE Transactions on Biomedical Engineering, vol. 58, No. 1, Jan. 2011.

(Continued)

*Primary Examiner* — Hadi Akhavannik
(74) *Attorney, Agent, or Firm* — CKC & Partners Co., LLC

(57) ABSTRACT

A non-contact heartbeat rate measurement system includes an image sensor, a target region selecting module, a heartbeat signal calculating module, a spectrum analyzing module, a vibration detecting module, a heartbeat peak selecting module. When a signal quality indicator is greater than a threshold value, and a first peak with global highest signal intensity in a heartbeat spectrum is similar to a face vibration frequency, the heartbeat peak selecting module selects a second peak with local highest signal intensity from a part frequency band of the heartbeat spectrum as an output heartbeat frequency. A non-contact heartbeat rate measurement method and an apparatus are disclosed herein.

22 Claims, 15 Drawing Sheets

(51) Int. Cl.
*G06T 7/00* (2017.01)
*G06T 7/90* (2017.01)
*A61B 5/11* (2006.01)
*A61B 5/00* (2006.01)

(52) U.S. Cl.
CPC .............. *G06T 7/0012* (2013.01); *G06T 7/90* (2017.01); *G06T 7/97* (2017.01); *A61B 5/0077* (2013.01); *A61B 2576/02* (2013.01); *G06T 2207/10016* (2013.01); *G06T 2207/10024* (2013.01); *G06T 2207/30201* (2013.01)

(56) References Cited

U.S. PATENT DOCUMENTS

| | | | | |
|---|---|---|---|---|
| 2012/0249287 A1* | 10/2012 | Levien | ............ | G09G 5/00 340/5.1 |
| 2015/0105670 A1* | 4/2015 | Bresch | ............ | A61B 5/0077 600/479 |
| 2015/0262338 A1* | 9/2015 | Xu | ............ | G06T 7/20 382/128 |
| 2015/0378433 A1* | 12/2015 | Savastinuk | ............ | G06F 21/32 345/156 |
| 2015/0379370 A1* | 12/2015 | Clifton | ............ | A61B 5/0075 382/128 |
| 2016/0106329 A1* | 4/2016 | Hoof | ............ | A61B 5/02416 600/479 |
| 2016/0183812 A1* | 6/2016 | Zhang | ............ | A61B 5/7246 600/301 |
| 2017/0007185 A1* | 1/2017 | Lin | ............ | A61B 5/1032 |
| 2018/0000359 A1* | 1/2018 | Watanabe | ............ | G06K 9/00906 |

FOREIGN PATENT DOCUMENTS

| | | |
|---|---|---|
| TW | M492140 U | 12/2014 |
| TW | I478690 B | 4/2015 |
| TW | 201517870 A | 5/2015 |
| TW | I527560 B | 4/2016 |
| TW | I548397 B | 9/2016 |
| TW | M564431 U | 8/2018 |
| WO | 2013128345 A1 | 9/2013 |

OTHER PUBLICATIONS

Gerard de Haan et al., "Robust pulse-rate from chrominance-based rPPG," IEEE Transactions on Biomedical Engineering, 2013.

\* cited by examiner

# NON-CONTACT HEARTBEAT RATE MEASUREMENT SYSTEM, METHOD AND APPARATUS THEREOF

CROSS-REFERENCE TO RELATED APPLICATION

This application claims priority to Taiwan Application Serial Number 107114076, filed Apr. 25, 2018, which is herein incorporated by reference in its entirety.

BACKGROUND

Technical Field

The present disclosure relates to a measurement system and a measurement method. More particularly, the present disclosure relates to a non-contact heartbeat measurement system and a non-contact heartbeat measurement method.

Description of Related Art

By measuring the heartbeat much important physiological information of human body can be obtained. The heartbeat measurement method in prior art is used by contact heartbeat measurement method, in other words, attaching the inductive patches to a respondent in order to measure the heartbeat signal of the respondent. However, the contact heartbeat measurement method in prior art induces the inconvenience and uncomfortableness to the respondent.

SUMMARY

The present disclosure provides a non-contact heartbeat measurement system in the present disclosure includes an image sensor, a target region selecting module, a heartbeat signal calculating module, a spectrum analyzing module, a vibration detecting module and a heartbeat peak selecting module. The image sensor is configured to capture a plurality of face images consecutively. The target region selecting module is configured to select a target region from each of the face images. The heartbeat signal calculating module is configured to calculate a color difference of each pixel of the target region in the face images captured in sequence in order to obtain a heartbeat signal. The spectrum analyzing module is configured to conduct the spectrum analysis of the heartbeat signal to obtain a heartbeat spectrum, the heartbeat spectrum including a plurality of intensity values of the heartbeat signal at a plurality of frequencies, and calculate a signal quality indicator of the heartbeat spectrum. The vibration detecting module is configured to detect, according to the face images, a face vibration frequency. When the heartbeat peak selecting module determines the signal quality indicator is greater than a threshold value and a first peak frequency with the global highest signal intensity in the heartbeat spectrum is similar to the face vibration frequency, the heartbeat peak selecting module selects a second peak frequency with a local highest signal intensity from a part frequency band of the heartbeat spectrum as the output heartbeat frequency.

According to some embodiments of the present disclosure, when the signal quality indicator is greater than a threshold value and a first peak frequency with a global highest signal intensity in the heartbeat spectrum is similar to the face vibration frequency, selecting a second peak frequency with a local highest signal intensity from a part frequency band of the heartbeat spectrum as the output heartbeat frequency is performed.

According to some embodiments of the present disclosure, when the signal quality indicator is greater than the threshold value and the first peak frequency with the global highest signal intensity in the heartbeat spectrum is different with the face vibration frequency, selecting the first peak frequency as the output heartbeat frequency is performed.

According to some embodiments of the present disclosure, when the signal quality indicator is lower than the threshold value, selecting a third peak frequency with a local highest signal intensity from the part frequency band of the heartbeat spectrum as the output heartbeat frequency is performed.

According to some embodiments of the present disclosure, the target region selecting module includes a feature point coordinate detecting element configured to detect a coordinate of mouth feature point and two coordinates of eye feature points in the face images and a target region frame selecting element configured to select, in accordance with the coordinate of mouth feature point and the coordinates of eye feature points, a frame for the target region.

According to some embodiments of the present disclosure, the non-contact heartbeat measurement system further includes a heartbeat change protection module configured to calculate a mean value and a standard deviation of the heartbeat frequency outputted each time by the heartbeat peak selecting module and generate, by performing the addition and subtraction of the mean value and the standard deviation, a boundary value, wherein if the output heartbeat frequency exceeds the boundary value, the boundary value is outputted, and if the output heartbeat frequency does not exceed the boundary value, the output heartbeat frequency is outputted.

According to some embodiments of the present disclosure, the non-contact heartbeat measurement system further includes an adaptive filter configured to remove the Gaussian noise and the measurement error of the boundary value or the output heartbeat frequency outputted by the heartbeat change protection module.

The present disclosure further provides a non-contact heartbeat measurement method in the present disclosure includes: capturing a plurality of face images consecutively, selecting a target region from each of the face images, obtaining a heartbeat signal in accordance with the color difference of each pixel of the target region in the face images captured in sequence, conducting the spectrum analysis of the heartbeat signal to obtain a heartbeat spectrum, the heartbeat spectrum comprising a plurality of intensity values of the heartbeat signal at a plurality of frequencies, calculating a signal quality indicator of the heartbeat spectrum, calculating a face vibration frequency according the face images, and selecting, based on the signal quality indicator and the face vibration frequency, one of the frequencies of the heartbeat spectrum as an output heartbeat frequency.

According to some embodiments of the present disclosure, the step of selecting the frequency in the heartbeat spectrum as the output heartbeat frequency includes, when the SNR is greater than a threshold value and a first peak frequency with a global highest signal intensity in the heartbeat spectrum is similar to the face vibration frequency, selecting a second peak frequency with a local highest signal intensity from a part frequency band of the heartbeat spectrum as the output heartbeat frequency.

According to some embodiments of the present disclosure, after the step of calculating, according to the face images, a face vibration frequency is performed, and the non-contact heartbeat rate measurement method further includes, when the signal quality indicator is greater than the threshold value and the first peak frequency with the global highest signal intensity in the heartbeat spectrum is different with the face vibration frequency, selecting the first peak frequency as the output heartbeat frequency.

According to some embodiments of the present disclosure, after the step of calculating, according to the face images, a face vibration frequency is performed, and the non-contact heartbeat rate measurement method further includes, when the signal quality indicator is lower than the threshold value, selecting a third peak frequency with a local highest signal intensity from a part frequency band of the heartbeat spectrum as the output heartbeat frequency.

According to some embodiments of the present disclosure, the step of selecting the target region from each of the face images includes detecting a coordinate of mouth feature point and two coordinates of eye feature points in the face images and selecting a frame for the target region in accordance with the coordinate of mouth feature point and coordinates of eye feature points.

The present disclosure further provides a non-contact heartbeat measurement apparatus which includes an image sensor and a calculation module. The image sensor is configured to capture a plurality of face images consecutively. The calculation module is coupled with the image sensor, wherein the calculation module is configured to select a target region from each of the face images, calculate a color difference of each pixel of the target region in the face images captured in sequence in order to obtain a heartbeat signal, conduct the spectrum analysis of the heartbeat signal to obtain a heartbeat spectrum including a plurality of intensity values of the heartbeat signal at a plurality of frequencies, calculate a signal quality indicator of the heartbeat spectrum, according to the face images calculate a face vibration frequency, and select a frequency from the frequencies of the heartbeat spectrum as an output heartbeat frequency in accordance with the signal quality indicator and the face vibration frequency.

According to some embodiments of the present disclosure, when the signal quality indicator is greater than a threshold value and a first peak frequency with a global highest signal intensity in the heartbeat spectrum is similar to the face vibration frequency, the calculation module selects a second peak frequency with a local highest signal intensity from a part frequency band of the heartbeat spectrum as the output heartbeat frequency.

According to some embodiments of the present disclosure, the non-contact heartbeat rate measurement apparatus further includes an output interface coupled with the calculation module and the image sensor, and configured to display the output heartbeat frequency and the face images.

According to some embodiments of the present disclosure, the non-contact heartbeat rate measurement apparatus further includes a battery module, a charge port, a power toggle button configured to switch an On/Off state of the non-contact heartbeat rate measurement apparatus, and a power supply module electrically connected to the battery module, the power toggle button, the image sensor and the calculation module, configured to selectively power, according to the On/Off status of the power toggle button, the image sensor and the calculation module.

According to some embodiments of the present disclosure, the non-contact heartbeat rate measurement apparatus includes a fastening module configured to fasten the non-contact heartbeat rate measurement apparatus on an external object.

The present disclosure further provides a non-contact heartbeat rate measurement system which includes an image sensor, a target region selecting module, a heartbeat signal calculating module, a spectrum analyzing module, an environment detecting module and a heartbeat peak selecting module. The image sensor is configured to capture a plurality of images consecutively, wherein the plurality of images comprise a plurality of face images and a plurality of background images. The target region selecting module is configured to select a target region from each of the plurality of face images. The heartbeat signal calculating module is configured to calculate a color difference of each pixel of the target region in the plurality of face images captured in sequence in order to obtain a heartbeat signal. The spectrum analyzing module is configured to conduct a spectrum analysis of the heartbeat signal to obtain a heartbeat spectrum. The heartbeat spectrum includes a plurality of intensity values of the heartbeat signal at a plurality of frequencies, and the spectrum analyzes module being further configured to calculate a signal quality indicator of the heartbeat spectrum. The environment detecting module is configured to detect an environment interference frequency of the change of the plurality of face images caused by the environment changing. The heartbeat peak selecting module is configured to select, in accordance with the signal quality indicator and the environment interference frequency, one of the plurality of frequencies of the heartbeat spectrum as an output heartbeat frequency.

According to some embodiments of the present disclosure, the environment detecting module includes a human face vibration detecting element configured to detect, according to the plurality of face images, a face vibration frequency.

According to some embodiments of the present disclosure, the environment detecting module further includes an environment illumination detecting element configured to detect, according to the plurality of background images, a background illumination change frequency.

According to some embodiments of the present disclosure, the environment detecting module further includes a camera vibration detecting element configured to detect, according to the plurality of background images, a camera vibration frequency.

According to some embodiments of the present disclosure, the environment detecting module further includes an environment illumination detecting element configured to detect, according to the plurality of background images, a background illumination change frequency.

DETAILED DESCRIPTION

The following embodiments are disclosed with accompanying diagrams for detailed description and ease of understanding. However, it should be understood that these details of the given embodiments do not intend to limit the present disclosure and the descriptions of construction operations do not limit the order of the execution. The equivalent constructions by reconfiguration of the components do not depart from the spirit and scope of the present disclosure.

It should be noted that the module illustrated in the present disclosure can be implemented with a circuit or a circuitry. The present disclosure is not limited thereto.

Figure 1:
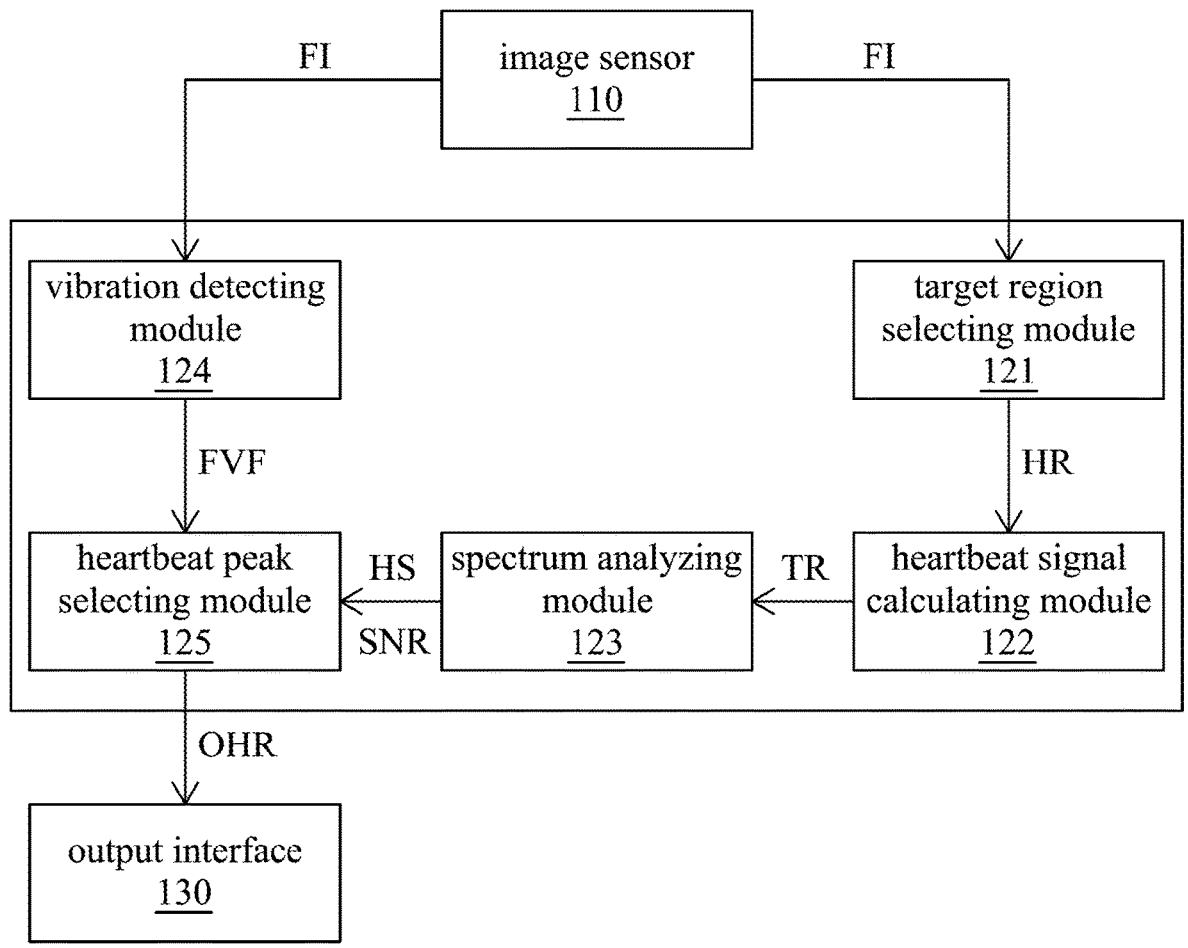
FIG. 1 is a function block diagram of a non-contact heartbeat measurement system, according to one embodiment of the present disclosure.
Figure 2:
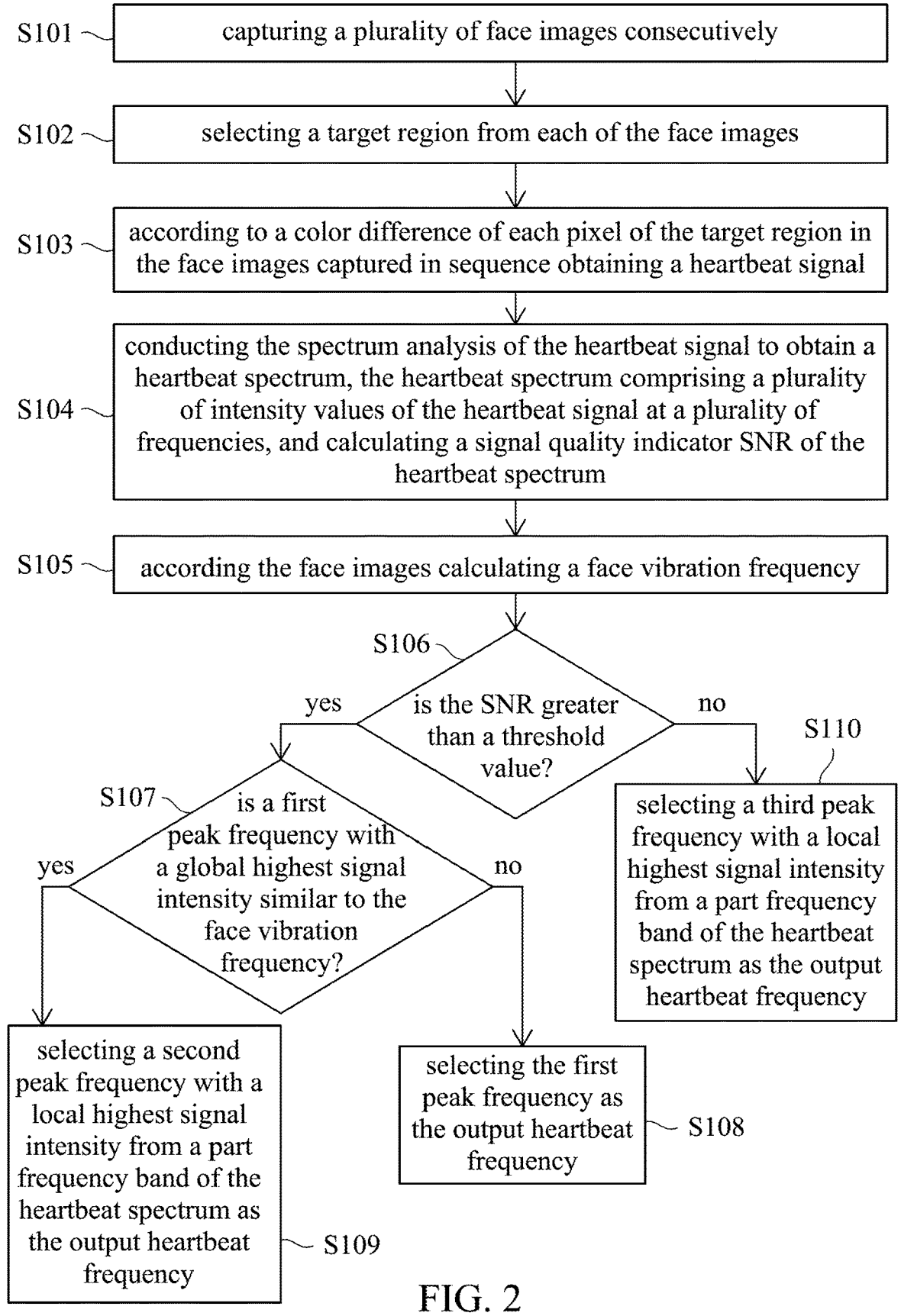
FIG. 2 is a flowchart of a non-contact heartbeat measurement method, according to one embodiment of the present disclosure.

Reference is made to FIG. 1 and FIG. 2. FIG. 1 is a function block diagram of a non-contact heartbeat measurement system 100, according to one embodiment of the present disclosure. FIG. 2 is a flowchart of a non-contact heartbeat measurement method M100, according to one embodiment of the present disclosure.

In this embodiment, the non-contact heartbeat rate measurement system 100 can be configured to execute the non-contact heartbeat rate measurement method M100 for non-contact heartbeat rate measurement, wherein the non-contact heartbeat rate measurement system 100 includes an image sensor 110, a target region selecting module 121, a heartbeat signal calculating module 122, a spectrum analyzing module 123, a vibration detecting module 124, a heartbeat peak selecting module 125 and an output interface 130. The non-contact heartbeat rate measurement method M100 includes the step S101 to S110. The image sensor 110 can be an optical sensor unit or a camera unit.

Figure 5A:
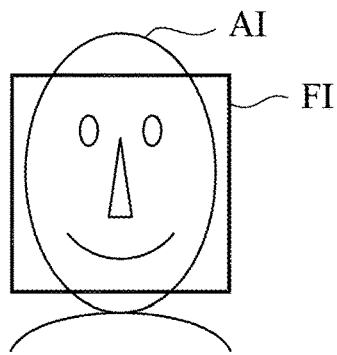
FIG. 5A is a schematic diagram of a face image, according to one embodiment of the present disclosure.

In the step S101, the image sensor 110 can capture a plurality of face images FI. Specifically, with reference to FIG. 5A, FIG. 5A is a schematic diagram of a face image, according to one embodiment of the present disclosure. The image sensor 110 firstly captures a whole image AI of the user. By applying the face detection technology, the face image FI in the whole image AI can be obtained, wherein the face detection technology can be a convolutional neural network (CNN), but the present disclosure is not limited thereto.

In one embodiment, the image sensor 110 can be a camera, a camcorder or a video tape recorder, etc.

In the step S102, the target region selecting module 121 selects a target region TR in the face image FI.

Figure 3:
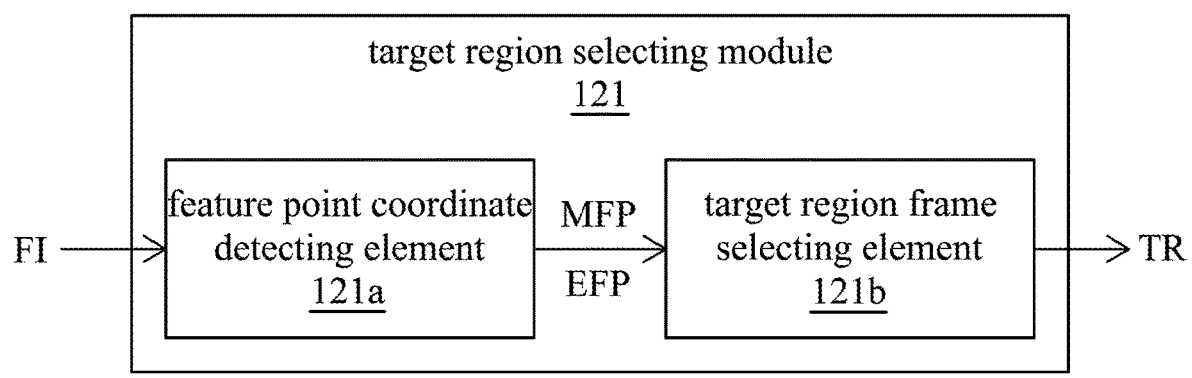
FIG. 3 is a further function block diagram of a target region selecting module of the non-contact heart rate measurement system, according to one embodiment of the present disclosure.
Figure 4:
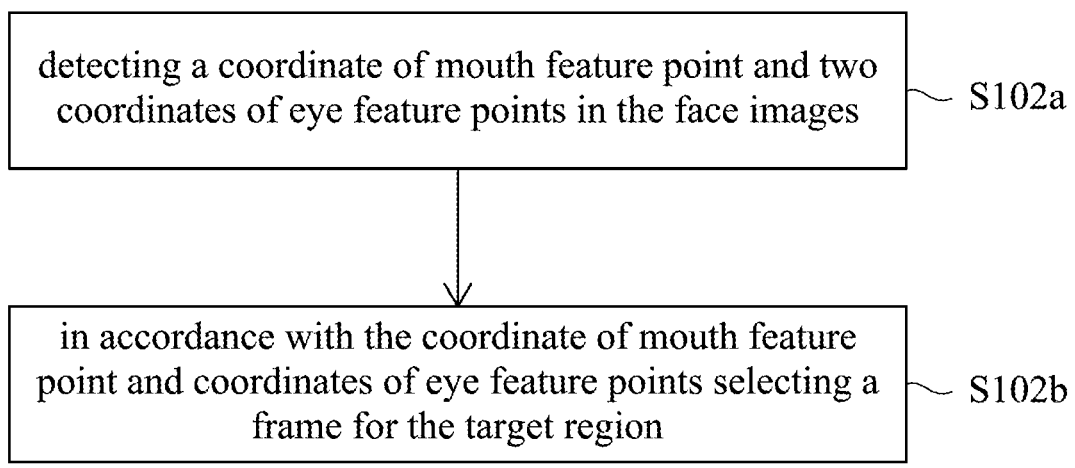
FIG. 4 is a further flowchart of the step S120 of the non-contact heartbeat measurement method, according to one embodiment of the present disclosure.
Figure 5B:
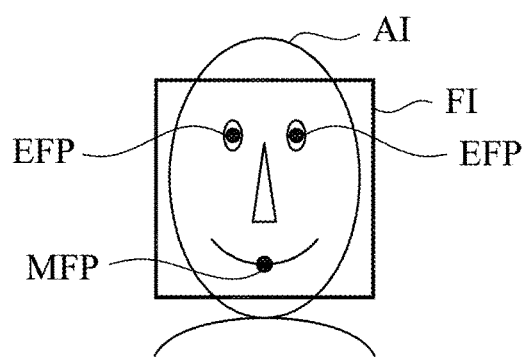
FIG. 5B is a schematic diagram of detecting the coordinate of mouth feature point and the coordinates of eye feature points in the face image shown in FIG. 5A, according to one embodiment of the present disclosure.
Figure 5C:
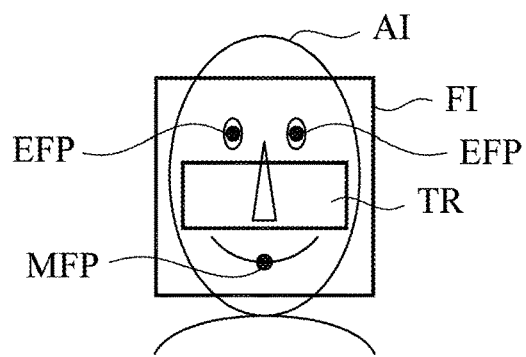
FIG. 5C is a schematic diagram of selecting a frame for the target region in the face image shown in FIG. 5B which is marked with the coordinate of mouth feature point and the coordinates of eye feature points, according to one embodiment of the present disclosure.

Furthermore, reference is made to FIG. 3, FIG. 4, FIG. 5B and FIG. 5C. FIG. 3 is a further function block diagram of the target region selecting module 121 of the non-contact heart rate measurement system 100, according to one embodiment of the present disclosure. FIG. 4 is a further flowchart of the step S120 of the non-contact heartbeat measurement method M100, according to one embodiment of the present disclosure. FIG. 5B is a schematic diagram of detecting the coordinate of mouth feature point MFP and the coordinates of eye feature points EFP in the face image FI shown in FIG. 5A. FIG. 5C is a schematic diagram of selecting a frame for the target region TR in the face image FI shown in FIG. 5B which is marked with the coordinate of mouth feature point MFP and the coordinates of eye feature points EFP.

As shown in FIG. 3, the target region selecting module 121 further includes a feature point coordinate detecting element 121a and a target region frame selecting element 121b. As shown in FIG. 4, the step S102 further includes the step S102a and the step S102b.

The feature point coordinate detecting element 121a, in accordance with the step S102a, detects the coordinate of mouth feature point MFP and the coordinates of eye feature points EFP (as shown in FIG. 5B) in the face image FI. Specifically, the feature point coordinate detecting element 121a can mark, according to the image feature (i.e., specific shape or specific color) of the mouth and the eyes, the mouth and the eyes in the face image FI and define the coordinates of the mouth and eyes respectively. Hereby the coordinate of mouth feature point MFP and the coordinates of eye feature points EFP are defined.

The target region frame selecting element 121b, in accordance with the step S102b, based on the coordinate of mouth feature point MFP and the coordinates of eye feature points EFP, selects a frame for the target region TR. Specifically, after defining the coordinate of mouth feature point MFP and the coordinates of eye feature points EFP, the target region frame selecting element 121b can select a frame for the target region TR between the coordinate of mouth feature point MFP and the coordinates of eye feature points EFP. For example, a middle point between the coordinates of mouth feature point MFP of the two corners of the mouth is a first middle point. A middle point between the coordinates of eye feature point EFP is a second middle point. The rectangular target region TR shown in FIG. 5C is selected as a frame with the middle point between the first middle point and the second middle point. Moreover, a low-pass filter is added to avoid huge fluctuation in the coordinate of mouth feature point MFP and the coordinates of eye feature points EFP in order to frame select the target region TR accurately.

In the step S103, the heartbeat signal calculating module 122 calculates a color difference of each pixel of the target region TR in the face images FI captured in sequence in order to obtain a heartbeat signal HR. Specifically, as shown in FIG. 6A, FIG. 6A is a schematic diagram of the heartbeat signal HR, according to one embodiment of the present disclosure, wherein the heartbeat signal HR has time domain representation, the horizontal axis being time with unit second (s) and vertical axis being intensity with unit decibel dB.

The heartbeat signal calculating module 122 calculates the target region TR captured in sequence with optical flow method to obtain the position of each pixel in the next moment. In detail, the red, green and blue signals of the corresponding pixel in the target region TR in the previous moment are subtracted from those in the next moment, respectively. The corresponding difference values in red, green and blue signals, which are indicated by difference values of red dR, the difference value of green dG, and difference value of blue dB, respectively can be obtained. Furthermore, the linear combination of the difference value of red dR, the difference value of green dG and the difference value of blue dB is performed. For instance, the difference value of red dR, the difference value of green dG and the difference value of blue dB are multiplied by a particular weight, and then added. Thereby the two groups of feature signal X and Y are obtained. Finally, taking an average for the difference values of each color in each pixel is performed, the heartbeat signal HR is thus obtained. In one embodiment, the heartbeat signal HR is used to indicate the variation of the difference value mentioned above in different time. Essentially the physics meaning of this application of the signal is equivalent to the Photoplethysmography (PPG). The conventional applications require wearing wearable devices such like a heartbeat belt and a hand band and lighting from specific light source at the same time. Because the intensity of reflection signal has high correlation with the blood volume of the skin, the variation of the intensity of reflection signal can be regarded as the heartbeat signal HR. This system uses the remote non-contact image sensor 110 to extract the heart signal HR from the small color variation of the reflection signal of the skin color for the ambient light source. In general, while the heart is contracting and relaxing, the blood pressure changes in capillaries. The face region is a region in which the capillaries are densely distributed, so that color of the face region may change slightly with the contraction and relaxation of the heart. The present disclosure provides the non-contact heart rate measurement module 122 to detect the color difference of the face region in order to detect the heartbeat signal HR.

In the step S104, the spectrum analyzing module 123 conducts a spectrum analysis with the heartbeat signal HR to obtain a heartbeat spectrum HS, the heartbeat spectrum HS including a plurality of intensity values of the heartbeat signal HR at a plurality of frequencies, and calculate a signal quality indicator SNR of the heartbeat spectrum. In general, as shown in FIG. 6B and FIG. 6C, FIG. 6B is a schematic diagram of the filtered heartbeat signal FHR which is the heartbeat signal HR shown in FIG. 6A passed through the band pass filter. FIG. 6C is a schematic diagram of the heartbeat spectrum HS produced by the spectrum analysis of the filtered heartbeat signal FHR shown in FIG. 6B.

Figure 6A:
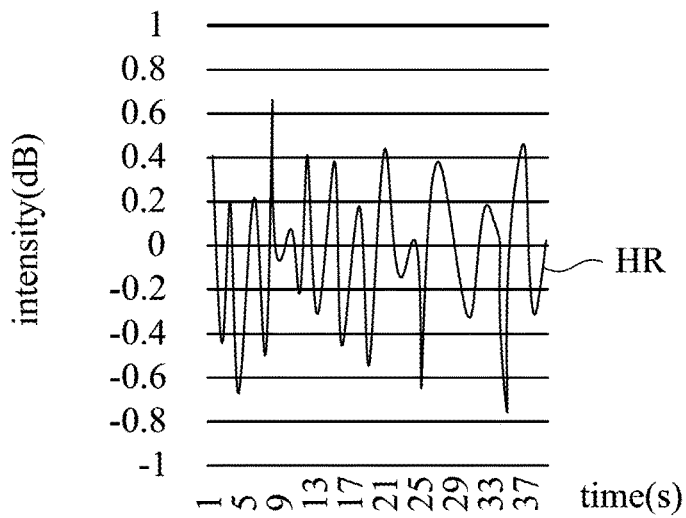
FIG. 6A is a schematic diagram of the heartbeat signal, according to one embodiment of the present disclosure.
Figure 6B:
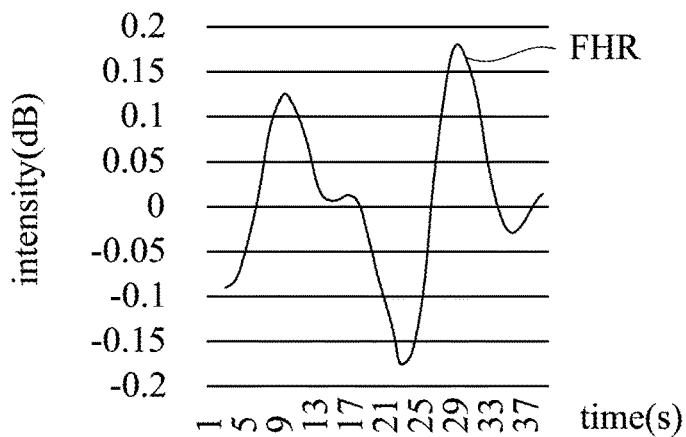
FIG. 6B is a schematic diagram of the filtered heartbeat signal which is the result of the heartbeat signal shown in FIG. 6A passing through the band pass filter, according to one embodiment of the present disclosure.
Figure 6C:
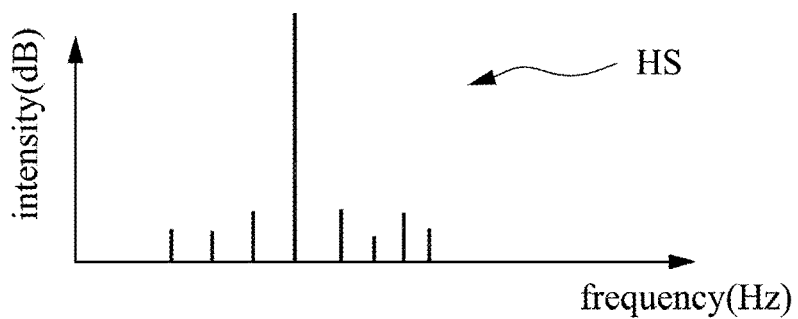
FIG. 6C is a schematic diagram of the heartbeat spectrum produced by the spectrum analysis of the filtered heartbeat signal shown in FIG. 6B, according to one embodiment of the present disclosure.

In detail, the spectrum analyzing module 123, as shown in FIG. 6A, filters the heartbeat signal HR every half second (about 15 frames) with the band pass filter and generates the filtered heartbeat signal FHR as shown in FIG. 6B. Moreover, the spectrum analyzing module 123 further performs the fast Fourier transform (FFT) with the filtered heartbeat signal FHR to thus obtain the heartbeat spectrum HS as shown in FIG. 6C. The heartbeat spectrum HS has frequency domain representation, in other words, horizontal axis being frequency with unit Hz and vertical axis being intensity with unit decibel dB. And the heartbeat spectrum HS includes a plurality of intensity values of the heartbeat signals at the frequencies. Furthermore, the spectrum analyzing module 123 calculates the signal quality indicator SNR of the heartbeat spectrum HS, wherein the signal quality indicator SNR is the ratio of the power of signal of heartbeat spectrum HS over the power of noise.

In the step S105, the vibration detecting module 124 detects, according to the face image FI, the face vibration frequency FVF. To be specific, the vibration detecting module 124 can calculate, according to the displacement of the coordinate of mouth feature point MFP and the coordinates of eye feature points EFP in the face images FI captured in sequence, the face vibration frequency FVF, and accompany with the speed compensation technique to reduce the face vibration frequency FVF.

In the step S106, the heartbeat peak selecting module 125 determines whether the signal quality indicator SNR of the heartbeat spectrum HS is greater than the threshold value, wherein the threshold value is set in accordance with the actual situation. For example, the threshold value of the SNR can be set to 0.8.

When the signal quality indicator SNR of the heartbeat spectrum HS is greater than the threshold value, for example, the signal quality indicator SNR of the heartbeat spectrum HS being 0.9, it indicates that the influence of face vibration frequency FVF on the heartbeat spectrum HS is too small to affect the heartbeat spectrum HS. The step S107 is performed.

In the step S107, the heartbeat peak selecting module 125 determines whether the first peak frequency PF1 with the global highest signal intensity in the heartbeat spectrum HS is similar to the face vibration frequency FVF.

When the first peak frequency PF1 with the global highest signal intensity in the heartbeat spectrum HS is different to the face vibration frequency FVF, it indicates that the first peak frequency PF1 with the global highest signal intensity is primarily and exactly produced by the heartbeat, not by the face vibration frequency FVF. The step S108 is performed.

Figure 7A:
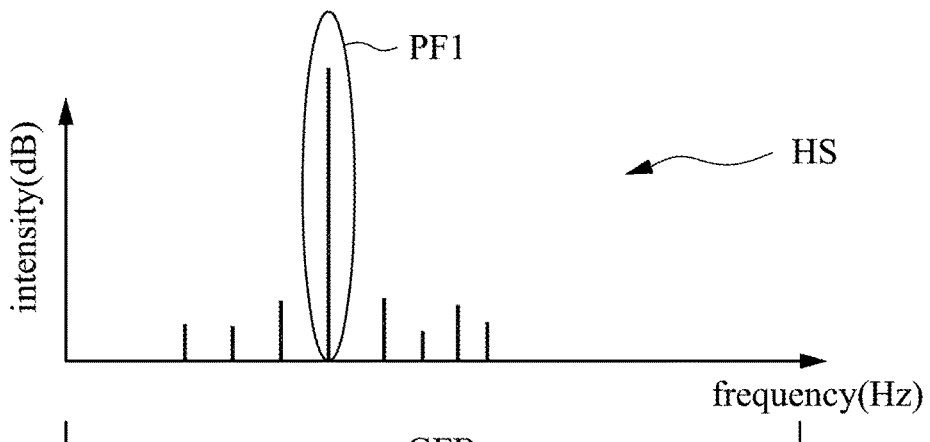
FIG. 7A is a schematic diagram of the first peak frequency as the output heart frequency, according to one embodiment of the present disclosure.

In the step S108, as shown in FIG. 7A, FIG. 7A is a schematic diagram of the first peak frequency PF1 as the output heart frequency OHR, according to one embodiment of the present disclosure. In other words, the heartbeat spectrum HS shown in FIG. 7A is the heartbeat spectrum HS which fulfills the condition that the signal quality indicator SNR is greater than the threshold value and the first peak frequency PF1 with the global highest signal intensity in the heartbeat spectrum HS is different with the face vibration frequency FVF.

Furthermore, it can be observed in FIG. 7A that the heartbeat spectrum HS in the global frequency band GFB includes a plurality of intensity values of the heartbeat signal at a plurality of frequencies, and the first peak frequency PF1 with the global highest signal intensity can be the output heartbeat frequency OHR and be outputted through the output interface 130, such like a projector or a display.

In another embodiment, when the first peak frequency PF1 with the global highest signal intensity in the heartbeat spectrum HS is similar to the face vibration frequency FVF, it indicates that the first peak frequency PF1 with the global highest signal intensity is primarily produced by the face vibration frequency FVF. The step S109 is performed.

Figure 7B:
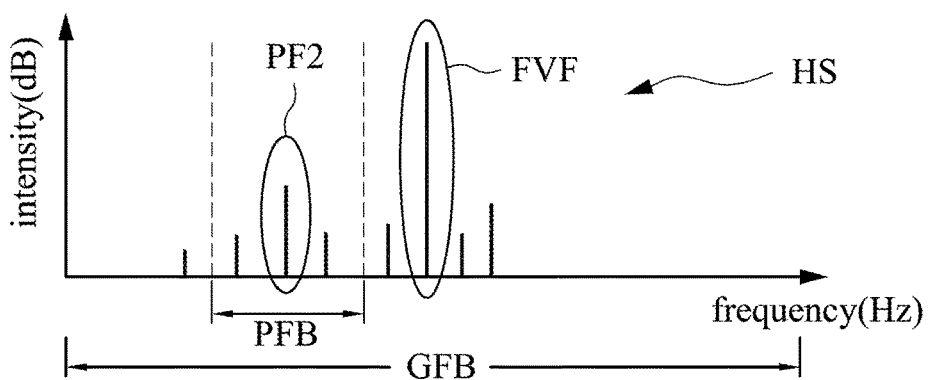
FIG. 7B is a schematic diagram of the second peak frequency as the output heart frequency, according to one embodiment of the present disclosure.

In the step S109, as shown in FIG. 7B, FIG. 7B is a schematic diagram of the second peak frequency PF2 as the output heart frequency OHR, according to one embodiment of the present disclosure. In other words, the heartbeat spectrum HS shown in FIG. 7B is the heartbeat spectrum which fulfills the condition that the signal quality indicator SNR is greater than the threshold value and the first peak frequency PF1 with the global highest signal intensity in the heartbeat spectrum HS is similar to the face vibration frequency FVF.

Furthermore, it can be observed in FIG. 7B that the heartbeat spectrum HS in the global frequency band GFB includes a plurality of intensity values of the heartbeat signal at a plurality of frequencies and the heartbeat spectrum HS includes the face vibration frequency FVF with the global highest signal intensity as well. In order to avoid directly mistaking the face vibration frequency FVF with the global highest signal intensity as the output heartbeat frequency OHR, the part frequency band PFB can be set in the global frequency band GFB, wherein the range of the part frequency band PFB is the range which meets the normal heartbeat frequency, such like 0.5 Hz to 4 Hz. Through this, the second peak frequency PF2 with the highest signal intensity in the part frequency band PFB can be the output heartbeat frequency OHR and be outputted through the output interface 130, such like a projector or a display.

In another embodiment, when the signal quality indicator SNR of the heartbeat spectrum HS is lower than the threshold value, for example, the signal quality indicator SNR of the heartbeat spectrum HS being 0.1, it indicates that the influence of face vibration frequency FVF on the heartbeat spectrum HS is so huge that affects the heartbeat spectrum HS. The step S110 is performed.

Figure 7C:
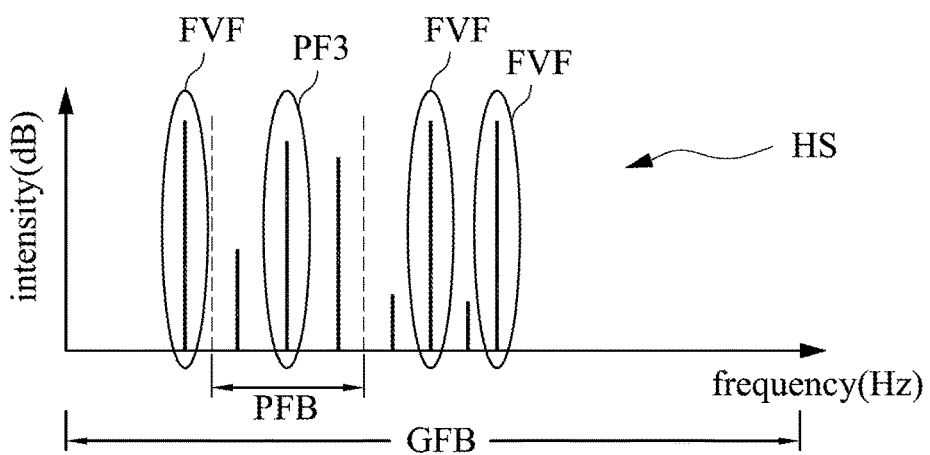
FIG. 7C is a schematic diagram of the third peak frequency as the output heart frequency, according to one embodiment of the present disclosure.

In the step S110, as shown in FIG. 7C, FIG. 7C is a schematic diagram of the third peak frequency PF3 as the output heart frequency OHF, according to one embodiment of the present disclosure. In other words, the heartbeat spectrum HS shown in FIG. 7C is the heartbeat spectrum HS which fulfills the condition that the signal quality indicator SNR is lower than the threshold value.

Furthermore, it can be observed in FIG. 7C that the heartbeat spectrum HS in the global frequency band GFB includes a plurality of intensity values of the heartbeat signal at a plurality the frequencies, and the heartbeat spectrum HS includes the face vibration frequency FVF with the global highest signal intensity as well. In order to avoid mistaking the face vibration frequency FVF with the global highest signal intensity as the output heartbeat frequency OHR, the part frequency band PFB is set in the global frequency band GFB, wherein the range of the part frequency band PFB is the range which meets the normal heartbeat frequency, such like 0.5 Hz to 5 Hz. Through this, the third peak frequency PF3 with the highest signal intensity in the part frequency band PFB can be the output heartbeat frequency OHR and be outputted through the output interface 130, such like a projector or a display.

It should be noticed that the target region selecting module 121, the feature point coordinate detecting element 121a, the target region frame selecting element 121b, the heartbeat signal calculating module 122, the spectrum analyzing module 123, the vibration detecting module 124 and the heartbeat peak selecting module 125 of the non-contact heartbeat rate measurement system 100 can be implemented with the hardware, software, firmware or the combination of hardware, software and firmware.

Referring back to FIG. 8, FIG. 8 is a function block diagram of the non-contact heartbeat measurement system 200, according to another embodiment of the present disclosure.

Figure 8:
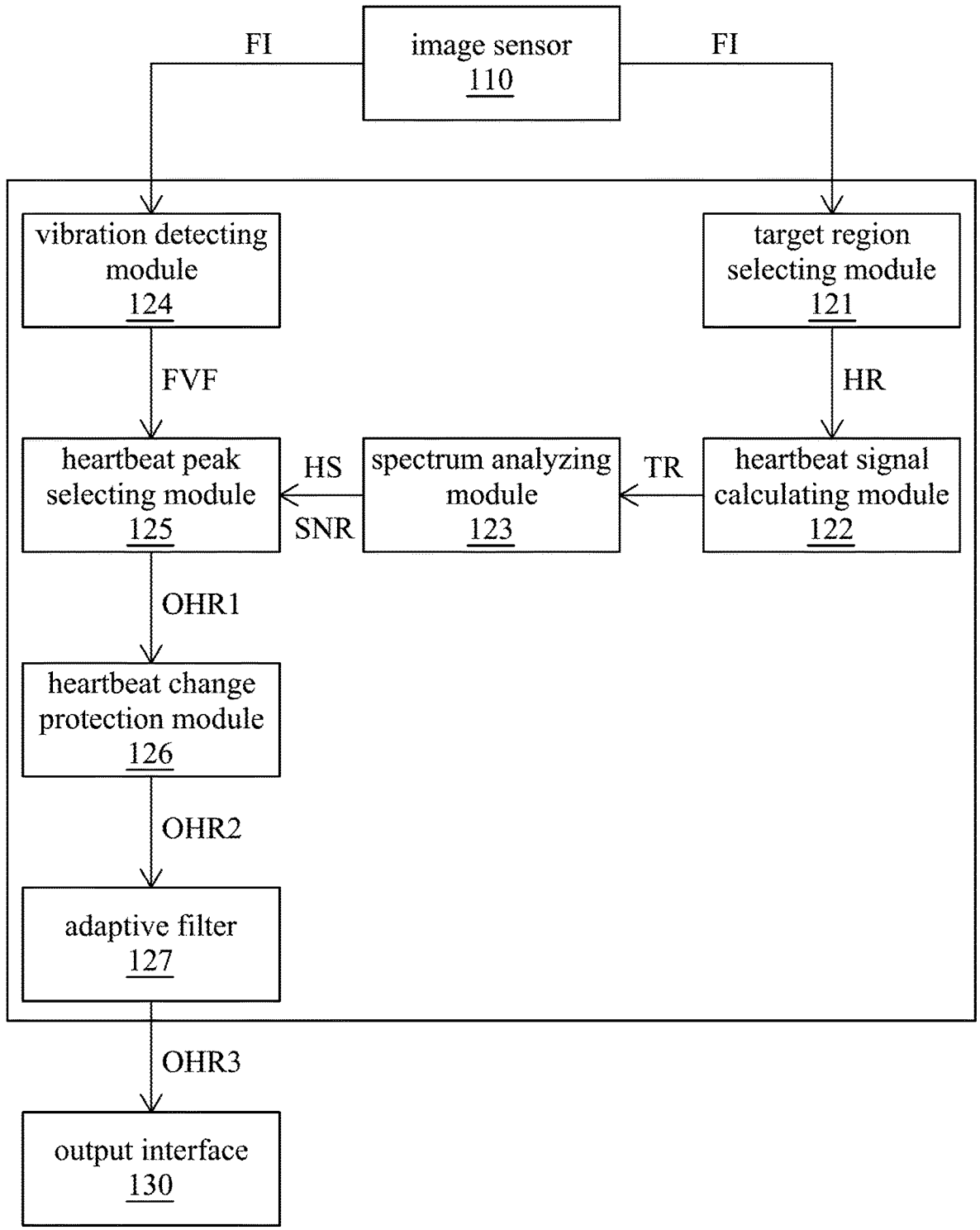
FIG. 8 is a function block diagram of a non-contact heartbeat measurement system, according to another embodiment of the present disclosure.

The non-contact heartbeat rate measurement system 200 as shown in FIG. 8 is similar to the non-contact heartbeat rate measurement system 100 shown in FIG. 1. The difference is the non-contact heartbeat rate measurement system 200 shown in FIG. 8 further includes the heartbeat change protection module 126 and the adaptive filter 127. In order to manifest the difference, the resemblance will not be described.

The heartbeat change protection module 126 is configured to calculate a mean value and a standard deviation of the first output heartbeat frequency OHR1 outputted by the heartbeat peak selecting module 125 each time, and generate, by performing the addition and subtraction of the mean value and the standard deviation, a boundary value. If the first output heartbeat frequency OHR1 exceeds the boundary value, the boundary value is outputted as the second output heartbeat frequency OHR2, and if the first output heartbeat frequency OHR1 does not exceed the boundary value, the first output heartbeat frequency OHR1 is outputted as the second output heartbeat frequency OHR2.

The adaptive filter 127 is configured to remove the Gaussian noise and the measurement error of the second output heartbeat frequency OHR2 outputted by the heartbeat change protection module 126 in order to output the third output heartbeat frequency OHR3. In this embodiment, the adaptive filter 127 is a Kalman filter, but the present disclosure is not limited thereto.

It should be noticed that the target region selecting module 121, the feature point coordinate detecting element 121a, the target region frame selecting element 121b, the heartbeat signal calculating module 122, the spectrum analyzing module 123, the vibration detecting module 124, the heartbeat peak selecting module 125, the heartbeat change protection module 126 and the adaptive filter 127 of the non-contact heartbeat rate measurement system 200 can be implemented with the hardware, software, firmware or the combination of hardware, software and firmware.

As the described above, the heartbeat peak selecting module 125 can, by determining two conditions that if the signal quality indicator SNR is greater than the threshold value and if the first peak frequency PF1 with the global highest signal intensity in the heartbeat spectrum HS is different with the face vibration frequency FVF and by correspondingly choosing the first peak frequency PF1, the second peak frequency PF2 or the third peak frequency PF3 to output the output heartbeat frequency OHR, further achieve the goal of motion robust heartbeat measurement. Furthermore, with the heartbeat change protection module 126 and the adaptive filter 127 as well the outputted heartbeat signal HR can be thus more stable.

Figure 9A:
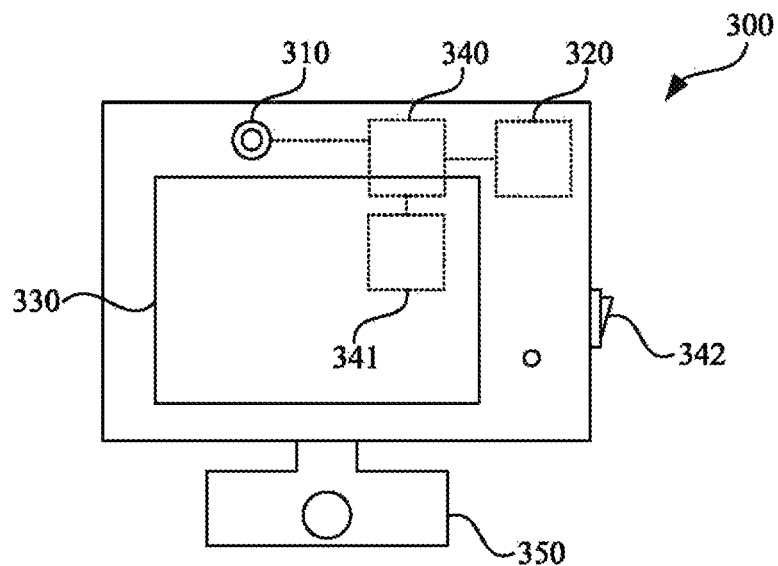
FIG. 9A is a front view of the non-contact heartbeat measurement apparatus, according to one embodiment of the present disclosure.
Figure 9B:
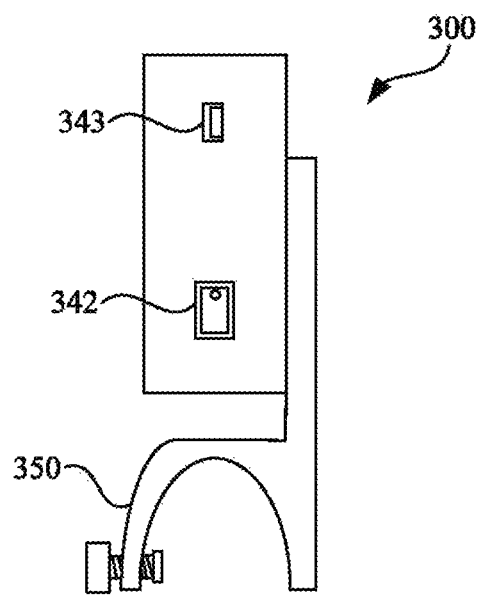
FIG. 9B is a side view of the non-contact heartbeat measurement apparatus shown in FIG. 9A.

Reference is made to FIG. 9A and FIG. 9B. FIG. 9A is a front view of the non-contact heartbeat measurement apparatus 300, according to one embodiment of the present disclosure. FIG. 9B is a side view of the non-contact heartbeat measurement apparatus 300 shown in FIG. 9A.

As shown in FIG. 9A, the non-contact heartbeat rate measurement apparatus 300 includes an image sensor 310 and a calculation module 320. The image sensor 310 can be an optical sensor unit or a camera element. The calculation module 320 can be an embedded physiological information calculation module, a processor, a specific application IC or any equivalent calculation circuit. In one embodiment, the calculation module 320 implements the target region selecting module 121, the heartbeat signal calculating module 122, the spectrum analyzing module 123, the vibration detecting module 124, and the heartbeat peak selecting module 125, the heartbeat change protection module 126 and the adaptive filter 127 described above in some previous embodiments (shown in FIG. 1 and FIG. 8) by the software, the firmware or the hardware.

The image sensor 310 is configured to capture a plurality of face images consecutively (referring to the face image FI in FIG. 5A to FIG. 5C). The calculation module 320 is coupled with the image sensor 310. In one embodiment, the calculation module 320 can be configured to execute the non-contact heartbeat rate measurement method M100 as described in previous embodiments (referring to FIG. 2 and the previous embodiments). The calculation module 320 selects a target region from each of the face images, calculates a color difference of each pixel of the target region in the face images captured in sequence in order to obtain a heartbeat signal, conducts the spectrum analysis of the heartbeat signal to obtain a heartbeat spectrum including a plurality of intensity values of the heartbeat signal at a plurality of frequencies, calculates a signal quality indicator of the heartbeat spectrum, according to the face images detects a face vibration frequency and in accordance with the signal quality indicator and the face vibration frequency selects a frequency from the frequencies of the heartbeat spectrum as an output heartbeat frequency. In one embodiment, when the signal quality indicator is greater than the threshold value and the first peak frequency with the global highest signal intensity in the heartbeat spectrum is similar to the face vibration frequency, the calculation module 320 selects the second peak frequency with the local highest signal intensity from the part frequency band of the heartbeat spectrum as the output heartbeat frequency.

The process and technical details of the calculation module 320 have been described in the step S101 to the step S109 of the previous embodiment (shown in FIG. 2), so it would not be elsewhere specified.

As shown in FIG. 9A, the non-contact heartbeat rate measurement apparatus 300 further includes the output interface 330, the output interface 330 coupled with the calculation module 320 and image sensor 310. The output interface 330 can be configured to display the output heartbeat frequency and the face images.

As shown in FIG. 9A and FIG. 9B, the non-contact heartbeat rate measurement apparatus 300 further includes a power supply module 340, a battery module 341, a power toggle button 342 and a charge port 343. The power supply module 340 and the battery module 341 are installed in the non-contact heartbeat rate measurement apparatus 300. In the embodiment in FIG. 9A and FIG. 9B, the power toggle button 342 and the charge port 343 are installed on the side of the non-contact heartbeat rate measurement apparatus 300. The power toggle button 342 is configured to switch an On/Off status of the non-contact heartbeat rate measurement apparatus 300. The charge port 343 is configured to be lapped to the matched power input (i.e., a transformer, a converter, etc., not shown in the figure). The power supply module 340 is electrically connected to the battery module 341, the power toggle button 342, the image sensor 310 and the calculation module 320, and configured to power, according to the On/Off status of the power toggle button 342, the image sensor 310 and the calculation module 320.

As shown in FIG. 9A and FIG. 9B, the non-contact heartbeat rate measurement apparatus 300 further includes a fastening module 350 to fasten the non-contact heartbeat rate measurement apparatus 300 on an external object (i.e., a wall, a table, a door frame, a pillar or relay, not shown in the figure). The fastening module 350 as shown in FIG. 9A and FIG. 9B is a clamp with a screw-lock structure, but the present disclosure is not limited thereto. In actual applications, the fastening module 350 can be a clamp with shrapnel, a buckle, a strap, an elastic collar or any other mechanical structure with equivalent fixing function.

In accordance with some embodiments in the present disclosure, the function of vibration detection can be substituted by the function of environment detection, including the function of human face vibration detection, camera vibration detection, and environment illumination detection.

Figure 10:
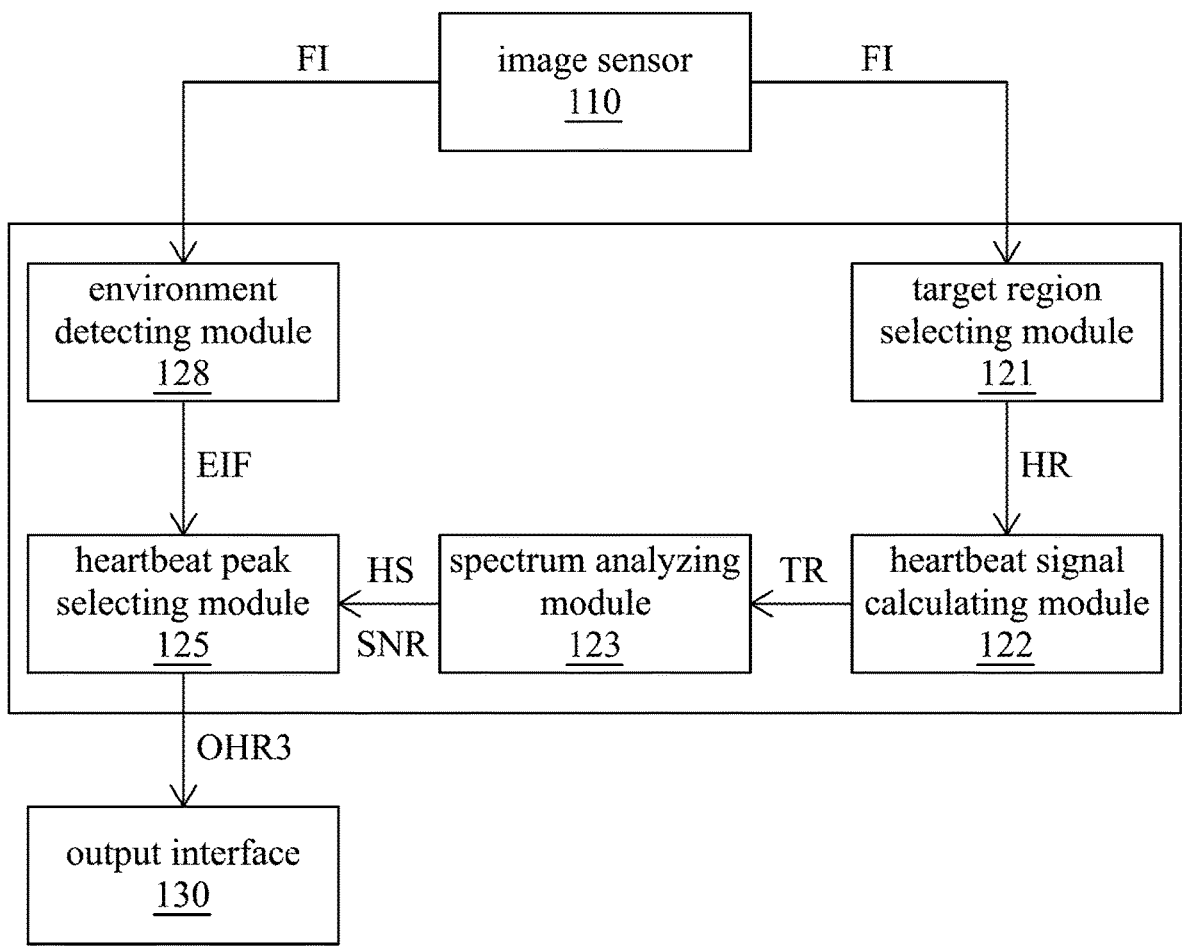
FIG. 10 is a function block diagram of a non-contact heartbeat measurement system, according to another embodiment of the present disclosure.

Please refer to the FIG. 10. FIG. 10 is a function block diagram of a non-contact heartbeat measurement system 400, according to another embodiment of the present disclosure. The non-contact heartbeat measurement system 400 shown in FIG. 10 is similar to the non-contact heartbeat measurement system 100 shown in FIG. 1. The difference is that the vibration detecting module 124 of the non-contact heartbeat measurement system 100 is replaced with the environment detecting module 128 in the non-contact heartbeat measurement system 400 shown in FIG. 10. The resemblance will not be discussed here.

Figure 11:
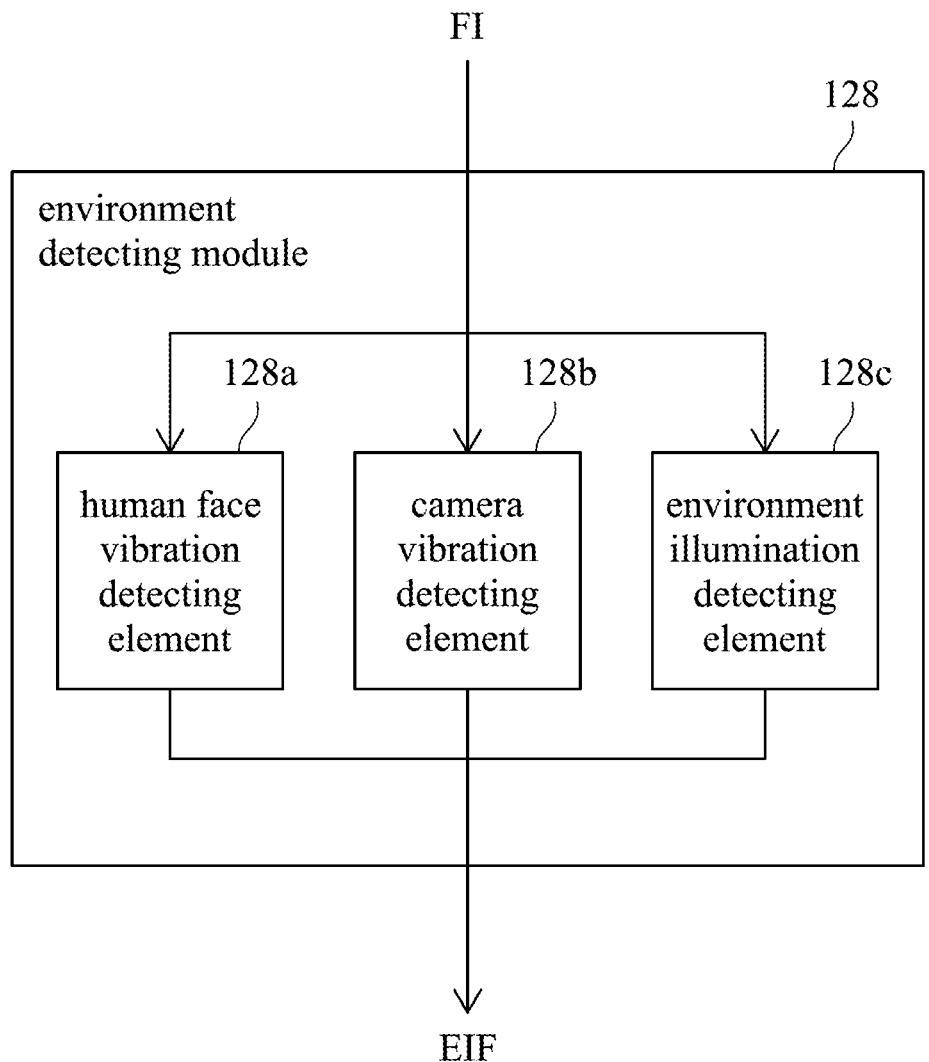
FIG. 11 is a function block diagram of an environment detecting module, according to another embodiment of the present disclosure.

Please refer to the FIG. 11. FIG. 11 is a function block diagram of an environment detecting module 128, according to another embodiment of the present disclosure. The environment detecting module 128 includes a human face vibration detecting element 128a, a camera vibration detecting element 128b and an environment illumination detecting element 128c. The environment detecting 128 is configured to detect a frequency of the change of the face images FI caused by the environment changing. The human face vibration detecting element 128a is configured to detect, according to the face images FI, the face vibration frequency FVF. The camera vibration detecting element 128b is configured to detect, according to background images, the camera vibration frequency. The environment illumination detecting element 128c is configured to detect, according to the background images, a background illumination change frequency. In one embodiment, the human face detecting element 128a, the camera vibration detecting element 128b and the environment illumination detecting element 128c can selectively execute separately, simultaneously or in pairs, according to the current implement situation.

Figure 12:
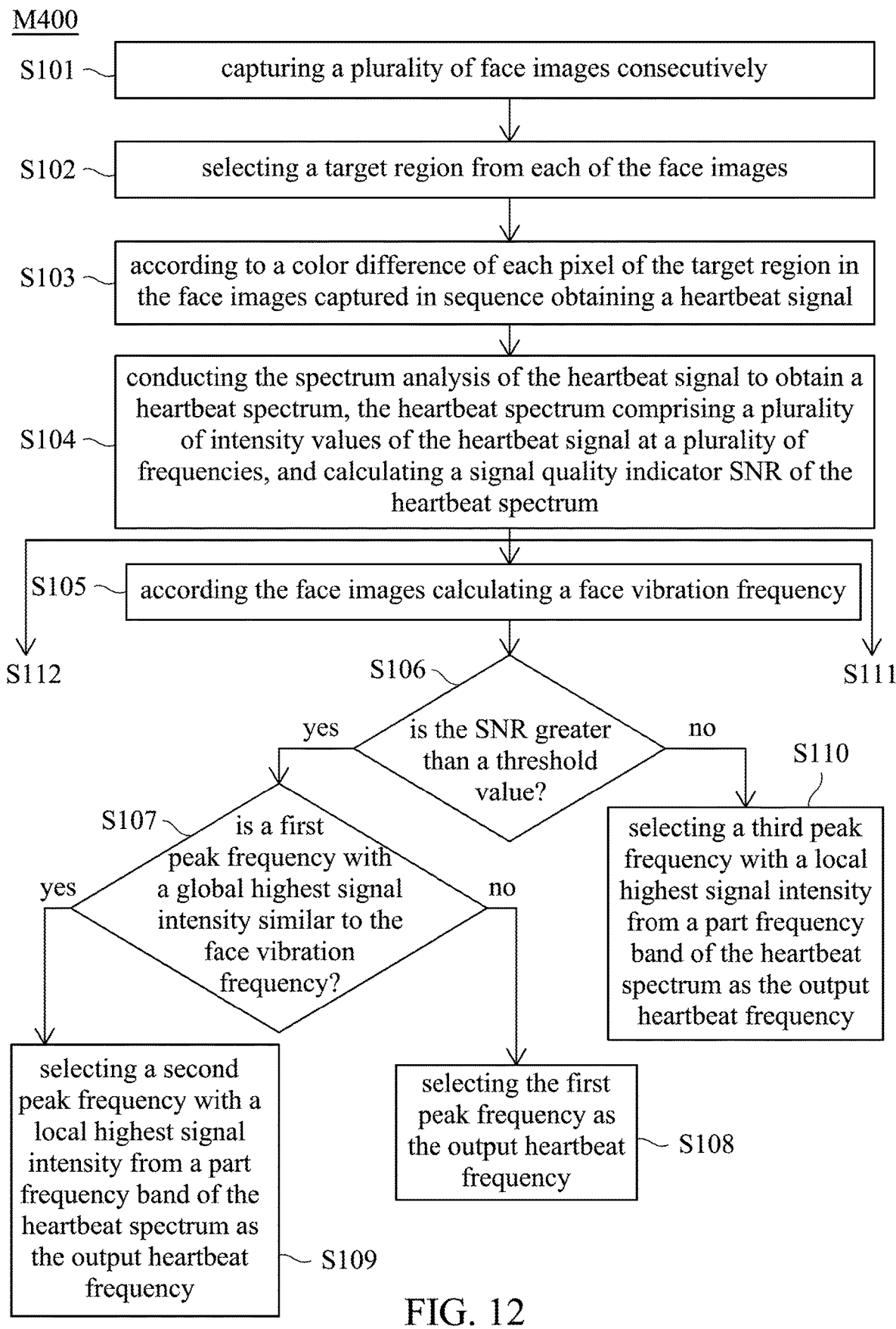
FIG. 12 is a flowchart of a non-contact heartbeat measurement method, according to another embodiment of the present disclosure.
Figure 13:
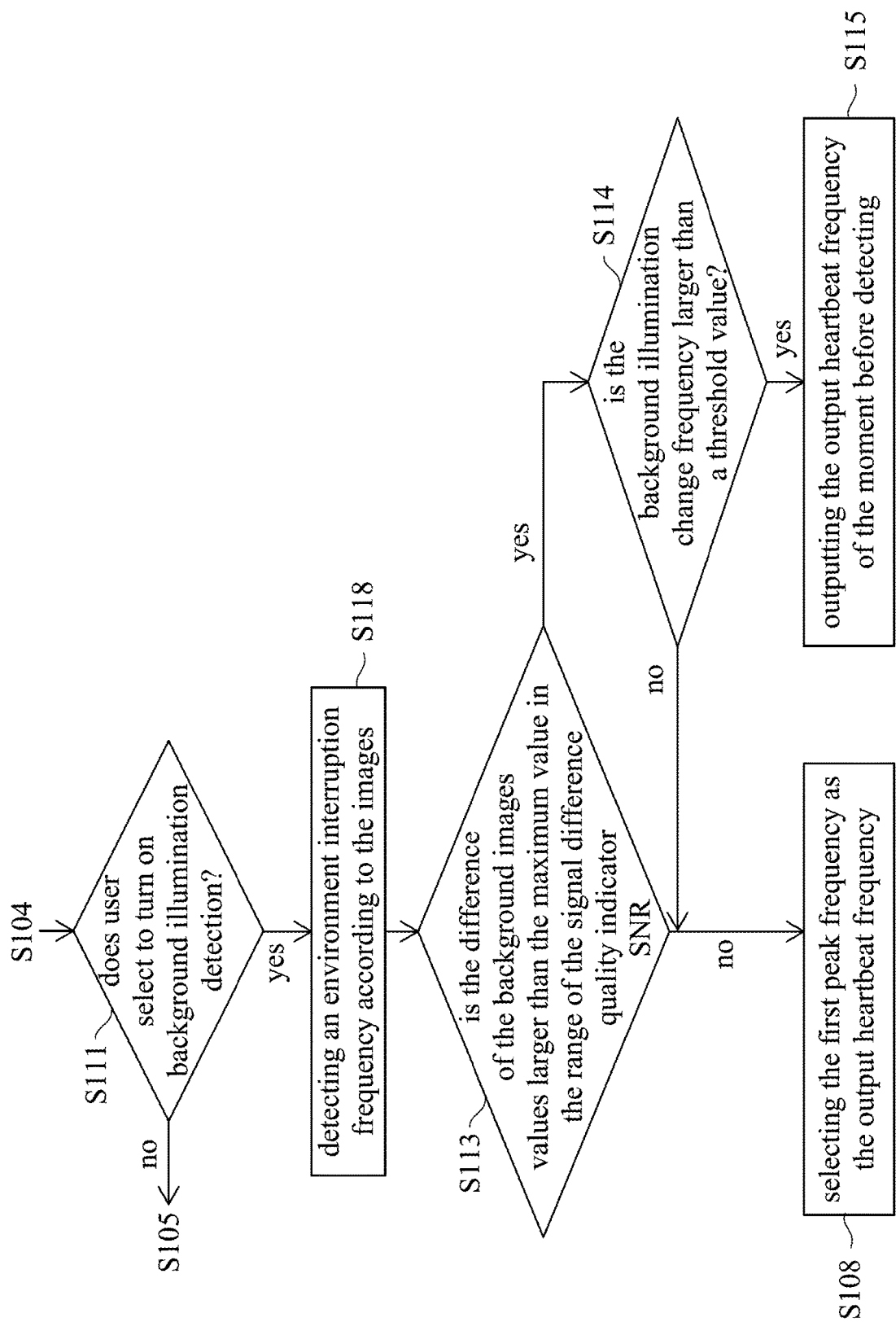
FIG. 13 is a partial flowchart of a non-contact heartbeat measurement method, according to another embodiment of the present disclosure.
Figure 14:
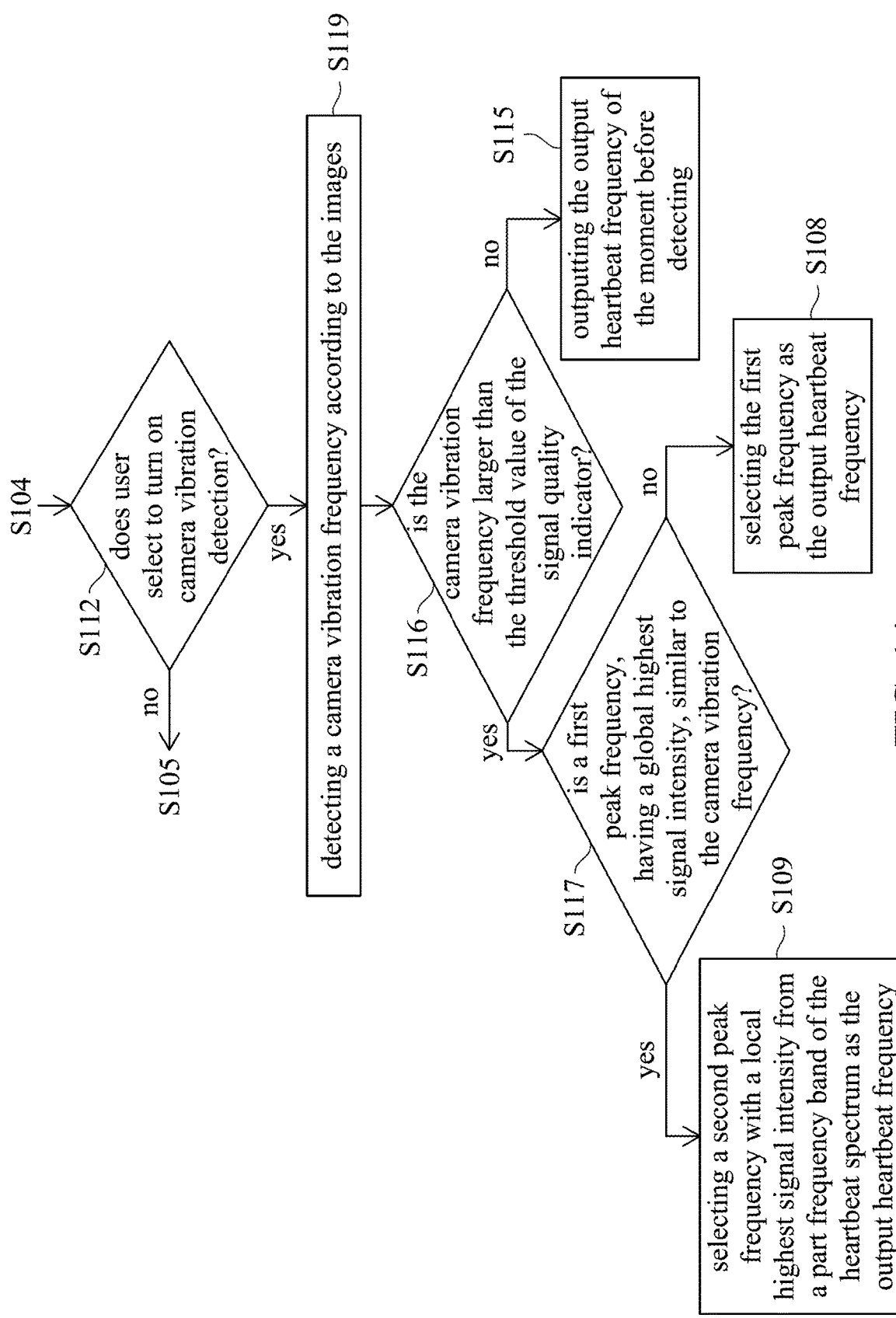
FIG. 14 is a partial flowchart of a non-contact heartbeat measurement method, according to another embodiment of the present disclosure.

Reference is now made to FIG. 12, FIG. 13 and FIG. 14 together. FIG. 12 is a flowchart of a non-contact heartbeat measurement method M400, according to another embodiment of the present disclosure. FIG. 13 and FIG. 14 are partial flowcharts of the non-contact heartbeat measurement method M400, according to another embodiment of the present disclosure. The non-contact heartbeat measurement method M400 shown in FIG. 12 is similar to the non-contact heartbeat measurement method M100 shown in FIG. 2. The difference is that by adding steps into the non-contact heartbeat measurement method M100 shown in FIG. 2, the non-contact heartbeat measurement method M400 includes the step S111, S113, S114, S115 and S118, related to illumination image value detecting, and the step S112, S115, S116, S117, S119, related to the camera vibration frequency.

It is noted that the step S111 in FIG. 13 and the step S112 in FIG. 14 are steps to determine whether the user selects to turn on the relevant functions. In other words, the steps S118 and S119 are steps to be performed selectively. The three steps S105, S118 and S119 in FIG. 12 can be performed simultaneously. The step S105 can be performed individually, the step S105 and step S118, or the step S105 and S119 can be performed in pairs.

In accordance with some embodiments in the present disclosure, when the user selects to turn on the functions of background illumination detection and background camera vibration detection, the steps S105, S118 and S119 are performed after the step S104. Reference is now made to FIG. 13, the step S111 is to determine whether the user turns on the function of background illumination detecting function. If it is "yes", the step S118 is performed. If it is "not", it is back to step S105. In step S118, a background illumination change frequency is detected according to images, the images including background images. And then, the step S113 is performed, it is determined whether the background image value is larger than the maximum value in the range of the signal difference quality indicator SNR. If it is "yes", the step S114 is performed. If it is "not", the step S112 is performed. The step S114 is to determine whether the background illumination change frequency is larger than a threshold value. If it is "yes", the step S115 is performed to output the output heartbeat frequency of the moment before detecting. If it is "not", the step S108 is performed.

Reference is now made to FIG. 14. The step S112 is to determine whether the user turns on the function of background camera vibration detection. If it is "yes", the step S119 is performed. If it is "not", it is back to step S105. The step S119 is to detect, according to the images, a camera vibration frequency, the images including the background images. Then, the step S116 is performed to determine whether the camera vibration frequency is larger than the threshold value of the signal quality indicator. If it is "yes", the step S117 is performed to determine whether a first peak frequency, having a global highest signal intensity, is similar to the camera vibration frequency. If it is "yes", the step S109 is performed. If it is "not", the step S108 is performed. If the result of the step S116 is "not", the step S115 is performed. The resemblance is not discussed here.

In accordance with some embodiments in the present disclosure, when the user selects to turn on the function of the background illumination detection, the steps S105 and S118 are performed simultaneously to detect the face vibration frequency and the background illumination change frequency. The succeeding steps are not discussed here.

In accordance with some embodiments in the present disclosure, when the user selects to turn on the function of the background camera vibration detection, the steps S105 and S119 are performed simultaneously to detect the face vibration frequency and the camera vibration frequency. The succeeding steps are not discussed here.

In accordance with some embodiments in the present disclosure, when the heartbeat peak selecting module 125 compares and determines that the signal quality indicator SNR is larger than a threshold value, and the first peak frequency, having the global highest signal intensity, of the heartbeat spectrum is similar to the face vibration frequency or the camera vibration frequency, the heartbeat peak selecting module 125 selects a second peak frequency, having a local highest signal intensity, in the partial frequency band of the heartbeat spectrum as the output heartbeat frequency. For detecting the background illumination change frequency of the background images in the images, two regions are selected respectively from each of an upper-left corner and an upper-right corner of the detected image. The size of the region is half of the size of the target region in the face images FI. The region is as the target for detecting. If the difference between the current background image value and the previous background image value is larger than the maximum value of the range of the signal difference quality, the counting mode is performed. When the change of frequency in a period of time is higher than a protection threshold indicator, the current heartbeat feature signal is the heartbeat feature signal of the period of time before the current counting mode is performed.

In accordance with some embodiments in the present disclosure, for preventing the first peak frequency of the environment detection overlapping with the face vibration frequency, the first peak frequency of the current face vibration frequency is kept during calculation, and the first peak frequency of the face vibration frequency of next moment is calculated first. By the difference between the spectrum of the heartbeat feature signals in sequence, the frequency of the current heartbeat feature signal is determined. If the first peak frequency of the face vibration frequency of the previous moment and the first peak frequency of the face vibration frequency of the next moment are on both sides of the background illumination change frequency to be calculated, the first peak frequency of the face vibration frequency of the previous moment is output as the output heartbeat frequency.

Figure 15:
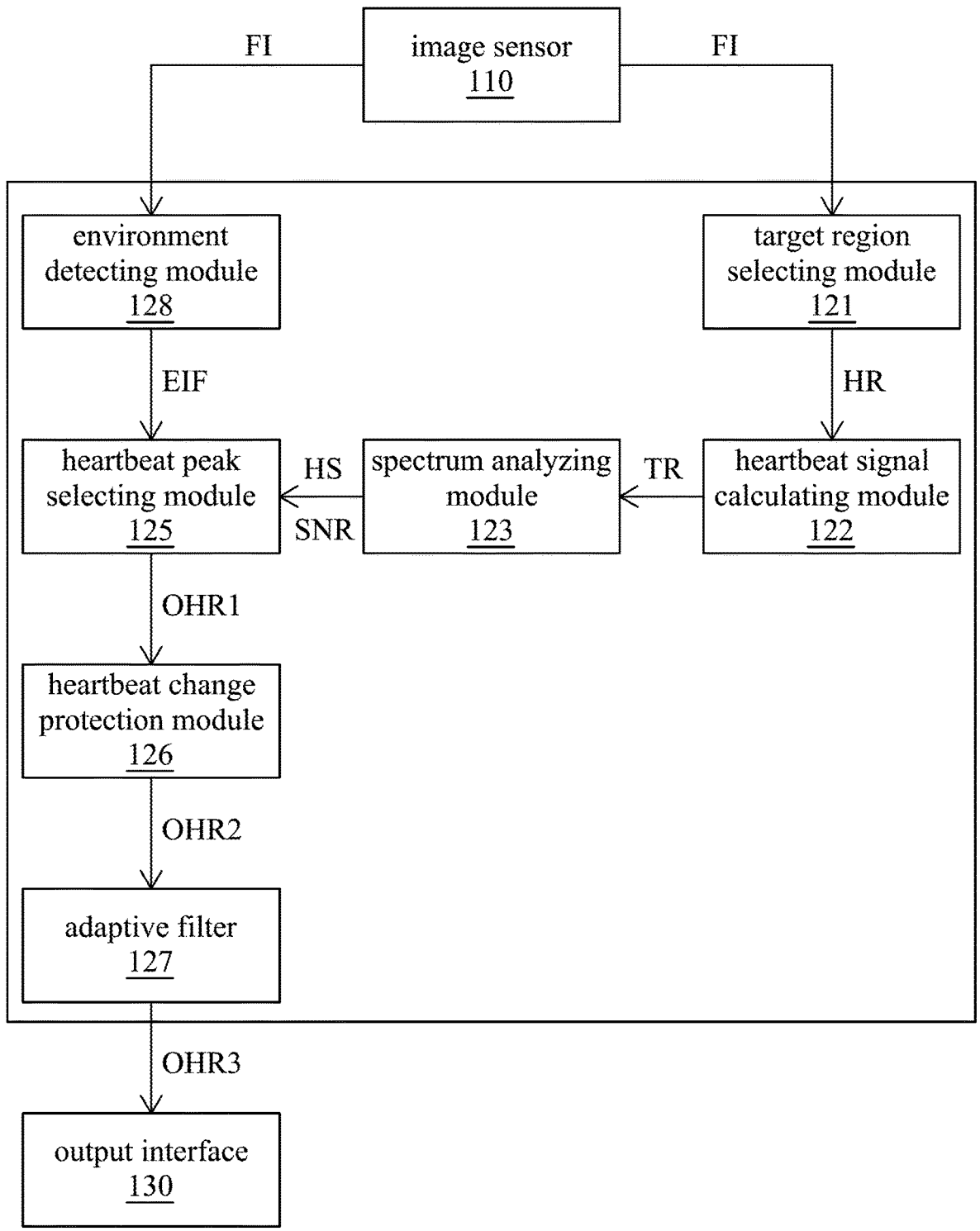
FIG. 15 is a function block diagram of a non-contact heartbeat measurement system, according to another embodiment of the present disclosure.

Reference is made to FIG. 15. FIG. 15 is a function block diagram of a non-contact heartbeat measurement system 500, according to another embodiment of the present disclosure. The non-contact heartbeat measurement system 500 shown in FIG. 15 is similar to the non-contact heartbeat measurement system 200 shown in FIG. 8. The difference is that the vibration detecting module 124 of the non-contact heartbeat measurement system 200 is replaced with the environment detecting module 128 in the non-contact heartbeat measurement system 500 shown in FIG. 15. The resemblance is not discussed here.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. A non-contact heartbeat rate measurement system, comprising:
    an image sensor configured to capture a plurality of face images consecutively;
    a target region selecting module configured to select a target region from each of the face images;
    a heartbeat signal calculating module configured to calculate a color difference of each pixel of the target region in the face images captured in sequence in order to obtain a heartbeat signal;
a spectrum analyzing module configured to conduct the spectrum analysis of the heartbeat signal to obtain a heartbeat spectrum, the heartbeat spectrum comprising a plurality of intensity values of the heartbeat signal at a plurality of frequencies, and the spectrum analyzing module being configured to calculate a signal quality indicator of the heartbeat spectrum;
a vibration detecting module configured to detect, according to the face images, a face vibration frequency; and
a heartbeat peak selecting module configured to select, in accordance with the signal quality indicator and the face vibration frequency, a frequency from the frequencies of the heartbeat spectrum as an output heartbeat frequency.

2. The non-contact heartbeat rate measurement system of claim 1, wherein when the signal quality indicator is greater than a threshold value and a first peak frequency with a global highest signal intensity in the heartbeat spectrum is similar to the face vibration frequency, selecting a second peak frequency with a local highest signal intensity from a part frequency band of the heartbeat spectrum as the output heartbeat frequency is performed.

3. The non-contact heartbeat rate measurement system of claim 1, wherein when the signal quality indicator is greater than the threshold value and the first peak frequency with the global highest signal intensity in the heartbeat spectrum is different with the face vibration frequency, selecting the first peak frequency as the output heartbeat frequency is performed.

4. The non-contact heartbeat rate measurement system of claim 1, wherein when the signal quality indicator is lower than the threshold value, selecting a third peak frequency with a local highest signal intensity from the part frequency band of the heartbeat spectrum as the output heartbeat frequency is performed.

5. The non-contact heartbeat rate measurement system of claim 1, wherein the target region selecting module comprises:
a feature point coordinate detecting element configured to detect a coordinate of mouth feature point and two coordinates of eye feature points in the face images; and
a target region frame selecting element configured to select, in accordance with the coordinate of mouth feature point and the coordinates of eye feature points, a frame for the target region.

6. The non-contact heartbeat rate measurement system of claim 1, further comprising:
a heartbeat change protection module configured to calculate a mean value and a standard deviation of the heartbeat frequency outputted each time by the heartbeat peak selecting module and generate, by performing the addition and subtraction of the mean value and the standard deviation, a boundary value, wherein if the output heartbeat frequency exceeds the boundary value, the boundary value is outputted, and if the output heartbeat frequency does not exceed the boundary value, the output heartbeat frequency is outputted.

7. The non-contact heartbeat rate measurement system of claim 6, further comprising:
an adaptive filter configured to remove the Gaussian noise and the measurement error of the boundary value or the output heartbeat frequency outputted by the heartbeat change protection module.

8. A non-contact heartbeat rate measurement method, comprising:
capturing a plurality of face images consecutively;
selecting a target region from each of the face images;
obtaining a heartbeat signal according to a color difference of each pixel of the target region in the face images captured in sequence;
conducting the spectrum analysis of the heartbeat signal to obtain a heartbeat spectrum, the heartbeat spectrum comprising a plurality of intensity values of the heartbeat signal at a plurality of frequencies, and calculating a signal quality indicator of the heartbeat spectrum;
calculating a face vibration frequency according to the face images; and
selecting a frequency from the frequencies of the heartbeat spectrum as an output heartbeat frequency in accordance with the signal quality indicator and the face vibration frequency.

9. The non-contact heartbeat rate measurement method of claim 8, wherein the step of selecting the frequency in the heartbeat spectrum as the output heartbeat frequency comprises:
when the SNR is greater than a threshold value and a first peak frequency with a global highest signal intensity in the heartbeat spectrum is similar to the face vibration frequency, selecting a second peak frequency with a local highest signal intensity from a part frequency band of the heartbeat spectrum as the output heartbeat frequency.

10. The non-contact heartbeat rate measurement method of claim 8, wherein after the step of calculating, according to the face images, a face vibration frequency is performed, the non-contact heartbeat rate measurement method further comprises:
when the signal quality indicator is greater than the threshold value and the first peak frequency with the global highest signal intensity in the heartbeat spectrum is different with the face vibration frequency, selecting the first peak frequency as the output heartbeat frequency.

11. The non-contact heartbeat rate measurement method of claim 8, wherein after the step of calculating, according to the face images, a face vibration frequency is performed, the non-contact heartbeat rate measurement method further comprises:
when the signal quality indicator is lower than the threshold value, selecting a third peak frequency with a local highest signal intensity from a part frequency band of the heartbeat spectrum as the output heartbeat frequency.

12. The non-contact heartbeat rate measurement method of claim 8, wherein the step of selecting the target region from each of the face images comprises:
detecting a coordinate of mouth feature point and two coordinates of eye feature points in the face images; and
selecting a frame for the target region in accordance with the coordinate of mouth feature point and coordinates of eye feature points.

13. A non-contact heartbeat rate measurement apparatus, comprising:
an image sensor configured to capture a plurality of face images consecutively; and
a calculation module coupled with the image sensor, and configured to select a target region from each of the face images, calculate a color difference of each pixel of the target region in the face images captured in sequence in order to obtain a heartbeat signal, conduct the spectrum analysis of the heartbeat signal to obtain a heartbeat spectrum comprising a plurality of intensity values of the heartbeat signal at a plurality of frequencies, calculate a signal quality indicator of the heartbeat spectrum, according the face images calculate a face vibration frequency, and in accordance with the signal quality indicator and the face vibration frequency select a frequency from the frequencies of the heartbeat spectrum as an output heartbeat frequency.

14. The non-contact heartbeat rate measurement apparatus of claim 13, wherein when the signal quality indicator is greater than a threshold value and a first peak frequency with a global highest signal intensity in the heartbeat spectrum is similar to the face vibration frequency, the calculation module selects a second peak frequency with a local highest signal intensity from a part frequency band of the heartbeat spectrum as the output heartbeat frequency.

15. The non-contact heartbeat rate measurement apparatus of claim 13, further comprising:
an output interface coupled with the calculation module and the image sensor, and configured to display the output heartbeat frequency and the face images.

16. The non-contact heartbeat rate measurement apparatus of claim 13, further comprising:
a battery module;
a charge port;
a power toggle button configured to switch an On/Off state of the non-contact heartbeat rate measurement apparatus; and
a power supply module electrically connected to the battery module, the power toggle button, the image sensor and the calculation module, configured to selectively power, according to the On/Off status of the power toggle button, the image sensor and the calculation module.

17. The non-contact heartbeat rate measurement apparatus of claim 13, further comprising:
a fastening module configured to fasten the non-contact heartbeat rate measurement apparatus on an external object.

18. A non-contact heartbeat rate measurement system, comprising:
an image sensor configured to capture a plurality of images consecutively, wherein the plurality of images comprise a plurality of face images and a plurality of background images;
a target region selecting module configured to select a target region from each of the plurality of face images;
a heartbeat signal calculating module configured to calculate a color difference of each pixel of the target region in the plurality of face images captured in sequence in order to obtain a heartbeat signal;
a spectrum analyzing module configured to conduct a spectrum analysis of the heartbeat signal to obtain a heartbeat spectrum, the heartbeat spectrum comprising a plurality of intensity values of the heartbeat signal at a plurality of frequencies, and the spectrum analyzing module being further configured to calculate a signal quality indicator of the heartbeat spectrum;
an environment detecting module configured to detect an environment interference frequency of the change of the plurality of face images caused by the environment changing; and
a heartbeat peak selecting module configured to select, in accordance with the signal quality indicator and the environment interference frequency, one of the plurality of frequencies of the heartbeat spectrum as an output heartbeat frequency.

19. The non-contact heartbeat rate measurement system of claim 18, wherein the environment detecting module comprises:
a human face vibration detecting element configured to detect, according to the plurality of face images, a face vibration frequency.

20. The non-contact heartbeat rate measurement system of claim 19, the environment detecting module further comprises:
a camera vibration detecting element configured to detect, according to the plurality of background images, a camera vibration frequency.

21. The non-contact heartbeat rate measurement system of claim 20, the environment detecting module further comprises:
an environment illumination detecting element configured to detect, according to the plurality of background images, a background illumination change frequency.

22. The non-contact heartbeat rate measurement system of claim 19, the environment detecting module further comprises:
an environment illumination detecting element configured to detect, according to the plurality of background images, a background illumination change frequency.

* * * * *